United States Patent [19]
Beard

[11] 3,979,404
[45] Sept. 7, 1976

[54] 2-SUBSTITUTED-1,2,4-THIADIAZOLO-[2,3-A]-IMIDAZOLES

[75] Inventor: Colin C. Beard, Palo Alto, Calif.

[73] Assignee: Syntex (U.S.A.) Inc., Palo Alto, Calif.

[22] Filed: Jan. 10, 1975

[21] Appl. No.: 540,023

Related U.S. Application Data

[62] Division of Ser. No. 403,473, Oct. 4, 1973, Pat. No. 3,901,903.

[52] U.S. Cl. .......................................... 260/306.8 F
[51] Int. Cl.² ..................................... C07D 417/14
[58] Field of Search ............................ 260/306.8 F

*Primary Examiner*—R. J. Gallagher
*Attorney, Agent, or Firm*—Gerard A. Blaufarb; William B. Walker

[57] ABSTRACT

Novel 2-substituted-1,2,4-thiadiazolo-[2,3-a]-imidazoles of the formula

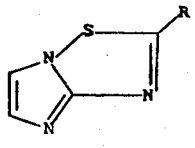

I and the pharmaceutically acceptable salts thereof; and process for their preparation. These 2-substituted-1,2,4-thiadiazolo-[2,3-a]-imidazoles are useful as fungistatic and fungicidal agents.

11 Claims, No Drawings

2-SUBSTITUTED-1,2,4-THIADIAZOLO-[2,3-A]-IMIDAZOLES

This is a division of application Ser. No. 403,473, filed Oct. 4, 1973, now U.S. Pat. No. 3,901,903, issued Aug. 26, 1975.

This invention relates to novel 2-substituted-1,2,4-thiadiazolo-[2,3-a]-imidazole compounds of the formula:

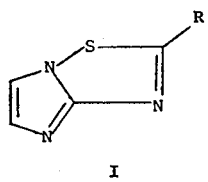

I wherein R is

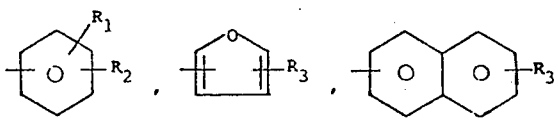

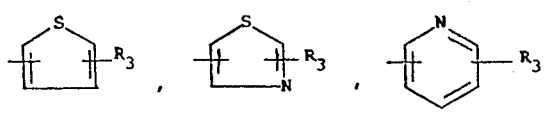

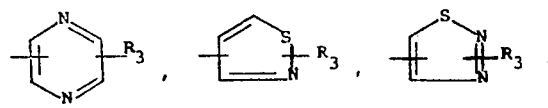

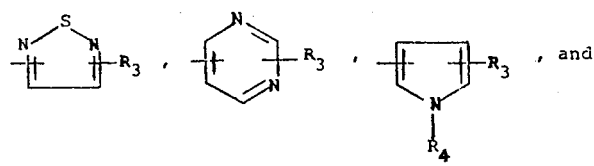

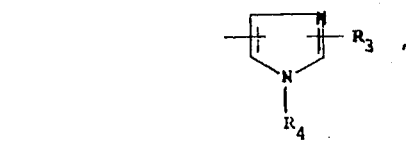

wherein
  $R_1$ and $R_2$ are each hydrogen, lower alkoxy, halo, nitro, lower alkyl, lower alkylthio, lower alkylsulfinyl, or trifluoromethyl;
  $R_3$ is hydrogen, lower alkoxy, halo, nitro, or lower alkyl; and
  $R_4$ is hydrogen or lower alkyl; and the pharmaceutically acceptable salts thereof, and processes for the preparation thereof.

The terms lower alkoxy, lower alkyl, lower alkylthio, and lower alkylsulfinyl as used above and in the claims are inclusive of moieties containing from 1 to 4 carbon atoms, for example, methyl, ethyl, propyl, isopropyl, butyl and tert.-butyl.

The term "halo" as used above and in the claims is inclusive of chloro, bromo, fluoro and iodo.

The compounds of Formula I are chemotherapeutic agents which possess fungistatic and fungicidal properties and thus are useful in combatting fungus infections.

Amongst the fungi against which the compounds of Formula I exhibit fungistatic and fungicidal activity are:

| | |
|---|---|
| M. andounini | H. gramineum |
| E. floccusum | M. gypsum |
| T. mentagrophytes | M. canis |
| C. albicans | T. rubrum |
| Cr. neoformans | T. tonsurans |
| R. solani | T. schoenleinii |
| A. solani | |

Particularly preferred are those compounds of Formula I wherein R is phenyl, 4-chlorophenyl, 4-methoxyphenyl, 4-methylphenyl, 4-methylthiophenyl, 4-methylsulfinylphenyl, 4-tert.-butylphenyl, 4-trifluoromethylphenyl, 2-furyl, 3-furyl, 2-naphthyl, 2-thienyl, 3-thienyl, 2-thiazolyl, 4-thiazolyl, 5-thiazolyl, 2-methyl-4-thiazolyl, 2-pyridyl, 3-pyridyl, 4-pyridyl, 2-pyrazinyl, 3-isothiazolyl, 4-isothiazolyl, 5-isothiazolyl, 1,2,3-thiadiazolyl, and 1,2,5-thiadiazolyl.

The compounds of Formula I are prepared according to the following generalized reaction scheme:

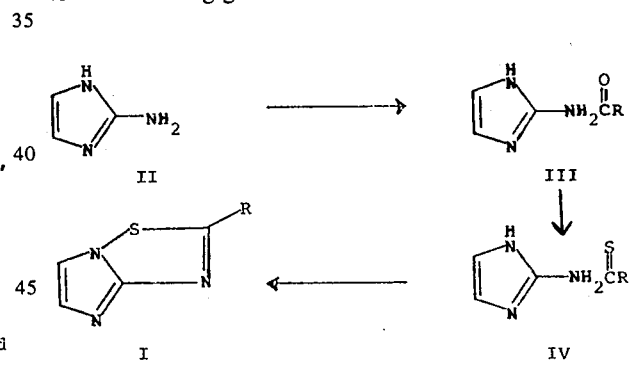

wherein R is defined as above.

The carbonylamino compounds of Formula III are obtained by treating the 2-aminoimidazole of Formula II, preferably as its hydrochloride, hydrobromide, or sulfate salt, with an acid chloride (RCOCl), acid ester (RCOOR$_5$, wherein R$_5$ is methyl or ethyl), or the mixed anhydride of a free acid (RCOOH) and trifluoroacetic acid.

The reaction of the compounds of Formula II with an acid chloride (RCOCL) to obtain the carbonylamino compounds of Formula III is carried out in the presence of an organic solvent, e.g., pyridine, acetone, tetrahydrofuran, and the like, at a temperature of from about −40° to 35°C. for from about 2 to 20 hours.

The reaction of the compound of Formula II with an acid ester (RCOOR$_5$) to obtain the carbonylamino compounds of Formula III is carried out at a temperature of from about 100° to 200°C. for from about 1 to 20 hours.

The reaction of the compound of Formula II with a mixed anhydride of a free acid (RCOOH) and trifluoroacetic acid, prepared from the free acid and trifluoroacetic acid anhydride, to obtain the carbonylamino compounds of Formula III is carried out in the presence of an inert organic solvent, e.g., tetrahydrofuran, acetone, and the like, and in the presence of a base, e.g., triethylamine, and the like, at a temperature of from about −20° to 30°C. for from about 1 to 20 hours.

The thus-obtained carbonylamino compounds of Formula III, obtained by reaction with an acid chloride, acid ester, or mixed anhydride, as described above, are then converted to the corresponding thionylcarbonylamino compounds of Formula IV by treatment with phosphorous pentasulfide ($P_2S_5$), in an inert organic solvent, e.g., pyridine, dioxane, and the like, at a temperature of from about 80° to 120°C., for from about 1 to 20 hours.

The 2-substituted 1,2,4-thiadiazolo-[2,3,-a]-imidazole compounds of Formula I are obtained by treating the compounds of Formula IV with sulfuryl chloride, in an inert organic solvent, e.g., chloroform, methylene chloride, and the like, at a temperature of from about 0° to 50°C., preferably 15° to 25°C., for from about 5 minutes to 6 hours, to obtain the 2-substituted-1,2,4-thiadiazolo-[2,3-a]-imidazole hydrochlorides, which upon treatment with a base, e.g., ammonia, sodium or potassium carbonate yield the corresponding free bases. The free base compounds of Formula I are, if desired, converted to their pharmaceutically acceptable salts by reaction with pharmaceutically acceptable acids, such as those set forth below, according to methods known to those skilled in the art.

Alternatively, other oxidizing agents, e.g., m-chloroperbenzoic acid, bromine, chlorine, peracetic acid, hydrogen peroxide, and the like, can be used in place of sulfuryl chloride, at a temperature of from about −40° to 40°C., for from about ¼ to 6 hours, in an inert organic solvent, e.g., chloroform, and the like, to treat the compounds of Formula IV. When the reaction is carried out using bromine or chlorine it is preferred that the temperature be between about 0° and 30°C. In addition, when the oxidation reaction is carried out using bromine or chlorine, the compounds of Formula I can, if desired, be isolated as their pharmaceutically acceptable hydrobromide or hydrochloride salts, or treated with a base, e.g., ammonia, sodium or potassium bicarbonate and the like, to obtain the corresponding free bases.

When the oxidation reaction is carried out using other than sulfuryl chloride, bromine or chlorine, the thus-obtained free bases of Formula I can be converted to their pharmaceutically acceptable salts by reaction with pharmaceutically acceptable acids, for example, inorganic acids, e.g., halogen hydroacids (particularly hydrochloric and hydrobromic), nitric acid, phosphoric acids, sulphonic acids, mono- and dicarboxylic acids, and the like; and organic acids, e.g., acetic, maleic, succinic, tartaric, lactic, citric, sorbic, salicylic, and the like.

The compounds of Formula I, or the pharmaceutically acceptable salts thereof, can be formulated into solutions, creams and ointments, according to methods known to those skilled in the art, for topical administration. Preferably a concentration of from about 0.5 to 5 percent of the active ingredient is used.

It is to be understood that isolation of the compounds described herein can be effected by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the examples described herein below. However, other equivalent separation or isolation procedures could, of course, also be used.

A further understanding of the invention can be had from the following non-limiting examples. Also, where necessary, examples are repeated to provide starting materials for subsequent examples.

EXAMPLE 1

A. To a suspension of 6.8 g. of 2-aminoimidazole hydrochloride in 100 ml. of pyridine at −20°C. there is added 6.8 ml. of benzoyl chloride. The thus-obtained reaction mixture is allowed to warm slowly to between 20°–30°C. (room temperature), and maintained at this temperature for 12 hours, diluted with water and filtered to give a residue which is recrystallized from methanol to yield 2-phenylcarbonylaminoimidazole [(III), R = phenyl].

Similarly, substituting a stoichiometric equivalent amount of
4-chlorobenzoyl chloride,
4-methoxybenzoyl chloride,
4-methylbenzoyl chloride,
4-methylthiobenzoyl chloride,
4-methylsulfinylbenzoyl chloride,
4-tert.-butylbenzoyl chloride,
4-trifluoromethylbenzoyl chloride,
2-furoyl chloride,
3-furoyl chloride,
2-naphthoyl chloride,
2-thenoyl chloride,
3-thenoyl chloride,
2-thiazoloyl chloride,
4-thiazoloyl chloride
5-thiazoloyl chloride,
2-methyl-4-thiazoloyl chloride,
2-pyridinoyl chloride,
3-pyridinoyl chloride,
4-pyridinoyl chloride,
2-pyrazinoyl chloride,
3-isothiazoloyl chloride,
4-isothiazoloyl chloride,
5-isothiazoloyl chloride,
1,2,3-thiadiazol-4-oyl chloride, and
1,2,5-thiadiazol-3-oyl chloride,
for 3-benzoyl chloride in the procedure of Example 1A, is productive of
2-(4-chlorophenylcarbonylamino)-imidazole,
2-(4-methoxyphenylcarbonylamino)-imidazole,
2-(4-methylphenylcarbonylamino)-imidazole,
2-(4-methylthiophenylcarbonylamino)-imidazole,
2-(4-methylsulfinylphenylcarbonylamino)-imidazole,
2-(4-tert.-butylphenylcarbonylamino)-imidazole,
2-(4-trifluoromethylphenylcarbonylamino)-imidazole,
2-(2-furylcarbonylamino)-imidazole,
2-(3-furylcarbonylamino)-imidazole,
2-(2-naphthylcarbonylamino)-imidazole,
2-(2-thienylcarbonylamino)-imidazole,
2-(3-thienylcarbonylamino)-imidazole,
2-(2-thiazolylcarbonylamino)-imidazole,
2-(4-thiazolylcarbonylamino)-imidazole,
2-(5-thiazolylcarbonylamino)-imidazole,
2-(2-methyl-4-thiazolylcarbonylamino)-imidazole, 2-(2-pyridylcarbonylamino)-imidazole,
2-(3-pyridylcarbonylamino)-imidazole,
2-(4-pyridylcarbonylamino)-imidazole,
2-(2pyrazinylcarbonylamino)-imidazole,
2-(3-isothiazolylcarbonylamino)-imidazole,
2-(4-isothiazolylcarbonylamino)-imidazole,
2-(5-isothiazolylcarbonylamino)-imidazole,
2-(1,2,3-thiadiazol-4-ylcarbonylamino)-imidazole, and
2-(1,2,5-thiadiazol-3-ylcarbonylamino)-imidazole, respectively.

B. To a solution of 3-furoic acid in 50 ml. of tetrahydrofuran, there is added 10.5 g. of trifluoroacetic anhydride. To the resulting solution, after 30 minutes and at 20°–25°C., there is added 15 ml. of triethylamine and 4.1 g. of 2-aminoimidazole hydrochloride and 20 ml. of tetrahydrofuran. The thus-obtained reaction mixture is allowed to stand overnight at 20°–25°C., followed by concentration, dilution with water, filtration and recrystallization from methanol to yield 2-(3-furylcarbonylamino)-imidazole [(III), R = 3-furyl], identical to that obtained in Example 1A.

EXAMPLE 2

A solution of 5 g. of 2-phenylcarbonylaminoimidazole [(III), R = phenyl] and 6 g. of phosphorous pentasulfide in 200 ml. of pyridine is heated in an oil bath at 100°–110°C. for eighteen hours. The bulk of the pyridine is removed under vacuum and the residue is treated with 500 ml. of saturated potassium bicarbonate solution, filtered and recrystallized from methanol to yield 2-phenylthiocarbonylaminoimidazole [(IV), R = phenyl].

Similarly, substituting a stoichiometric equivalent amount of the other compounds obtained in Example 1A (or Example 1B) for 2-phenylcarbonylaminoimidazole, and following the procedure of Example 2 is productive of
2-(4-chlorophenylthiocarbonylamino)-imidazole,
2-(4-methoxphenylthiocarbonylamino)-imidazole,
2-(4-methylphenylthiocarbonylamino)-imidazole,
2-(4-methylthiophenylthiocarbonylamino)-imidazole,
2-(4-methylsulfinylphenylthiocarbonylamino)-imidazole,
2-(4-tert.-butylphenylthiocarbonylamino)-imidazole,
2-(4-trifluoromethylphenylthiocarbonylamino)-imidazole,
2-(2-furylthiocarbonylamino)-imidazole,
2-(3-furylthiocarbonylamino)-imidazole,
2-(2-naphthylthiocarbonylamino)-imidazole,
2-(2-thienylthiocarbonylamino)-imidazole,
2-(3-thienylthiocarbonylamino)-imidazole,
2-(2-thiazolylthiocarbonylamino)-imidazole,
2-(4-thiazolylthiocarbonylamino)-imidazole,
2-(5-thiazolylthiocarbonylamino)-imidazole,
2-(2-methyl-4-thiazolylthiocarbonylamino)-imidazole,
2-(2-pyridylthiocarbonylamino)-imidazole,
2-(3-pyridylthiocarbonylamino)-imidazole, and
2-(4-pyridylthiocarbonylamino)-imidazole,
2-(2-pyrazinylthiocarbonylamino)-imidazole,
2-(3-isothiazolylthiocarbonylamino)-imidazole,
2-(4-isothiazolylthiocarbonylamino)-imidazole, and
2-(5-isothiazolylthiocarbonylamino)-imidazole,
2-(1,2,3-thiadiazol-4-ylthiocarbonylamino)-imidazole, and
2-(1,2,5-thiadiazol-3-ylthiocarbonylamino)-imidazole, respectively.

EXAMPLE 3

A. To 0.21 g. of 2-(4-thiazolylthiocarbonylamino)-imidazole [(IV) R = 4-thiazolyl], dissolved in 10 ml. of chloroform at 20°–25°C. (room temperature), there is added dropwise 0.09 ml. of sulfuryl chloride in 5 ml. of chloroform. After 2 hours, the reaction mixture is filtered and the residue of 2-(4-thiazolyl)-1,2,4-thiadiazolo-[2,3-a]-imidazole hydrochloride is treated with 50 ml. of chloroform and 50 ml. of aqueous ammonia. The chloroform layer is separated, dried over magnesium sulfate, and concentrated. The product is recrystallized from methanol to yield 2-(4-thiazolyl)-1,2,4-thiadiazolo-[2,3-a]-imidazole [(I), R = 4-thiazolyl].

Similarly, substituting a stoichiometric equivalent amount of other compounds obtained in Example 2,
2-phenylthiocarbonylaminoimidazole,
2-(4-chlorophenylthiocarbonylamino)-imidazole,
2-(4-methoxyphenylthiocarbonylamino)-imidazole,
2-(4-methylphenylthiocarbonylamino)-imidazole,
2-(4-methylthiophenylthiocarbonylamino)-imidazole,
2-(4-methylsulfinylthiocarbonylamino)-imidazole,
2-(4-tert.-butylphenylthiocarbonylamino)-imidazole,
2-(4-trifluoromethylphenylthiocarbonylamino)-imidazole,
2-(2-furylthiocarbonylamino)-imidazole,
2-(3-furylthiocarbonylamino)-imidazole,
2-(2-naphthylthiocarbonylamino)-imidazole,
2-(2-thienylthiocarbonylamino)-imidazole,
2-(3-thienylthiocarbonylamino)-imidazole,
2-(2-thiazolylthiocarbonylamino)-imidazole,
2-(5-thiazolylthiocarbonylamino)-imidazole,
2-(2-methyl-4-thiazolylthiocarbonylamino)-imidazole,
2-(2-pyridylthiocarbonylamino)-imidazole,
2-(3-pyridylthiocarbonylamino)-imidazole,
2-(4-pyridylthiocarbonylamino)-imidazole,
2-(2-pyrazinylthiocarbonylamino)-imidazole,
2-(3-isothiazolylthiocarbonylamino)-imidazole,
2-(4-isothiazolylthiocarbonylamino)-imidazole,
2-(5-isothiazolylthiocarbonylamino)-imidazole,
2-(1,2,3-thiadiazol-4-ylthiocarbonylamino)-imidazole,
2-(1,2,5-thiadiazol-3-ylthiocarbonylamino)-imidazole,
for 2-(4-thiazolyl)-thiocarbonylaminoimidazole in the procedure of Example 3 is productive of
2-phenyl-1,2,4-thiadiazolo-[2,3,-a]-imidazole,
2-(4-chlorophenyl)-1,2,4-thiadiazolo-[2,3-a]-imidazole,
2-(4-methoxyphenyl)-1,2,4-thiadiazolo-[2,3-a]-imidazole,
2-(4-methylphenyl)-1,2,4-thiadiazolo-[2,3-a]-imidazole,
2-(4-methylthiophenyl)-1,2,4-thiadiazolo-[2,3-a]-imidazole,
2-(4-methylsulfinylphenyl)-1,2,4-thiadiazolo-[2,3-a]-imidazole,
2-(4-tert.-butylphenyl)-1,2,4-thiadiazolo-[2,3-a]-imidazole,
2-(4-trifluoromethylphenyl)-1,2,4-thiadiazolo-[2,3-a]-imidazole,
2-(2-furyl)-1,2,4-thiadiazolo-[2,3-a]-imidazole,
2-(3-furyl)-1,2,4-thiadiazolo-[2,3-a]-imidazole,
2-(2-naphthyl)-1,2,4-thiadiazolo-[2,3-a]-imidazole,
2-(2-thienyl)-1,2,4-thiadiazolo-[2,3-a]-imidazole,
2-(3-thienyl)-1,2,4-thiadiazolo-[2,3-a]-imidazole,
2-(2-thiazolyl)-1,2,4-thiadiazolo-[2,3-a]-imidazole,
2-(5-thiazolyl)-1,2,4-thiadiazolo-[2,3-a]-imidazole, 2-(2-methyl-4-thiazolyl)-1,2,4-thiadiazolo-[2,3-a]-imidazole,
2-(2-pyridyl)-1,2,4-thiadiazolo-[2,3-a]-imidazole,
2-(3-pyridyl)-1,2,4-thiadiazolo-[2,3-a]-imidazole,
2-(4-pyridyl)-1,2,4-thiadiazolo-[2,3-a]-imidazole,
2-(2-pyrazinyl)-1,2,4-thiadiazolo-[2,3-a]-imidazole,
2-(3-isothiazolyl)-1,2,4-thiadiazolo-[2,3-a]-imidazole,
2-(4-isothiazolyl)-1,2,4-thiadiazolo-[2,3-a]-imidazole,
2-(5-isothiazolyl)-1,2,4-thiadiazolo-[2,3-a]-imidazole,
2-(1,2,3-thiadiazol-4-yl)-1,2,4-thiadiazolo-[2,3-a]-imidazole,
and
2-(1,2,5-thiadiazol-3-yl)-1,2,4-thiadiazolo-[2,3-a]-imidazole, respectively.

B. To a solution of 0.4 g. of 2-phenylthiocarbonylaminoimidazole [(IV), R = phenyl] in 20 ml. of chloroform there is added dropwise, at 20°–25°C., a solution of 0.165 ml. of sulfuryl chloride in 5 ml. of chloroform. After two hours the precipitate which forms is filtered, dissolved in methanol, and precipitated from ether to yield 2-phenyl-1,2,4-thiadiazolo-[2,3-a]-imidazole hydrochloride.

C. To a solution of 0.19 g. of 2-(2-furylthiocarbonylamino)-imidazole [(IV), R = 2-furyl] in 25 ml. of chloroform, at 20°–25°C, there is added dropwise 0.09 ml. of sulfuryl chloride in 5 ml. of chloroform. After four hours, the reaction mixture is chilled in ice, followed by filtration to yield 2-(2-furyl)-1,2,4-thiadiazolo-[2,3-a]-imidazole hydrochloride.

D. To 0.2 g. of 2-(3-furylthiocarbonylamino)-imidazole [(IV), R = 3-furyl] in 10 ml. of chloroform, at 20°–25°C, there is added dropwise 0.1 ml. of sulfuryl chloride in 2 ml. of chloroform. After 10 minutes the reaction mixture is concentrated at 10°–20°C. under vacuum to give a residue which is treated with methanol and filtered. The residue obtained following filtration is treated with dilute aqueous ammonia to give a precipitate which is filtered and dried to yield 2-(3-furyl)-1,2,4-thiadiazolo-[2,3-a]-imidazole.

In the examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound represented by the formula:

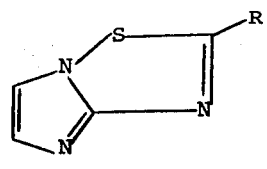

I wherein R is

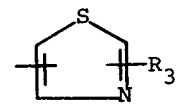,

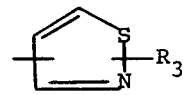,

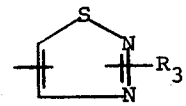, and

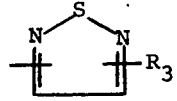, in which $R_3$ is hydrogen, lower alkoxy, halo, nitro, or lower alkyl; and the pharmaceutically acceptable salts thereof.

2. A compound of claim 1 wherein R is 2-thiazolyl, 4-thiazolyl, 5-thiazolyl, 2-methyl-4-thiazolyl, 3-isothiazolyl, 4-isothiazolyl, 5-isothiazolyl, 1,2,3-thiadiazol-4-yl and 1,2,5-thiadiazol-3-yl.

3. The compound of claim 2 wherein R is 2-thiazolyl, 2-(2-thiazolyl)-1,2,4-thiadiazolo-[2,3-a]-imidazole.

4. The compound of claim 2 wherein R is 4-thiazolyl, 2-(4-thiazolyl)-1,2,4-thiadiazolo-[2,3-a]-imidazole.

5. The compound of claim 2 wherein R is 5-thiazolyl, 2-(5-thiazolyl)-1,2,4-thiadiazolo-[2,3-a]-imidazole.

6. The comound of claim 2 wherein R is 2-methyl-4-thiazolyl, 2-(2-methyl-4-thiazolyl)-1,2,4-thiadiazolo-[2,3-a]-imidazole.

7. The compound of claim 2 wherein R is 3-isothiazolyl, 2-(3-isothiazolyl)-1,2,4-thiadiazolo-[2,3-a]-imidazole.

8. The compound of claim 2 wherein R is 4-isothiazolyl, 2-(4-isothiazolyl)-1,2,4-thiadiazolo-[2,3-a]-imidazole.

9. The compound of claim 2 wherein R is 5-isothiazolyl, 2-(5-isothiazolyl)-1,2,4-thiadiazolo-[2,3-a]-imidazole.

10. The compound of claim 2 wherein R is 1,2,3-thiadiazol-4-yl, 2-(1,2,3-thiadiazol-4-yl)-1,2,4-thiadiazolo-[2,3-a]-imidazole.

11. The compound of claim 2 wherein R is 1,2,5-thiadiazol-3-yl, 2-(1,2,5-thiadiazol-3-yl)-1,2,4-thiadiazolo-[2,3-a]-imidazole.

* * * * *